(12) United States Patent
Moffitt et al.

(10) Patent No.: US 8,649,873 B2
(45) Date of Patent: Feb. 11, 2014

(54) DEEP BRAIN STIMULATION CURRENT STEERING WITH SPLIT ELECTRODES

(71) Applicant: Boston Scientific Neuromodulation Corporation, Valencia, CA (US)

(72) Inventors: Michael Adam Moffitt, Valencia, CA (US); Thomas A. Oleksyn, Valencia, CA (US); Kerry Bradley, Glendale, CA (US); David Karl Lee Peterson, Valencia, CA (US); Courtney Lane, Ventura, CA (US); Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/920,986

(22) Filed: Jun. 18, 2013

(65) Prior Publication Data

US 2013/0289651 A1 Oct. 31, 2013

Related U.S. Application Data

(63) Continuation of application No. 12/761,622, filed on Apr. 16, 2010, now Pat. No. 8,473,061.

(60) Provisional application No. 61/170,037, filed on Apr. 16, 2009, provisional application No. 61/316,759, filed on Mar. 23, 2010.

(51) Int. Cl.
*A61N 1/00* (2006.01)
(52) U.S. Cl.
USPC .......................................................... 607/45
(58) Field of Classification Search
USPC .......................................................... 607/45
See application file for complete search history.

(56) References Cited

U.S. PATENT DOCUMENTS

| 4,602,624 A | 7/1986 | Naples et al. |
| 4,630,611 A | 12/1986 | King |

(Continued)

FOREIGN PATENT DOCUMENTS

| EP | 0580928 A1 | 2/1994 |
| EP | 0650694 B1 | 7/1998 |

(Continued)

OTHER PUBLICATIONS

Official Communication for U.S. Appl. No. 13/665,533 mailed Jun. 13, 2013.

(Continued)

*Primary Examiner* — Robert N Wieland
(74) *Attorney, Agent, or Firm* — Frommer Lawrence & Haug LLP; Bruce E. Black

(57) ABSTRACT

A device for brain stimulation includes a lead having a longitudinal surface, a proximal end, a distal end and a lead body. The device also includes a plurality of electrodes disposed along the longitudinal surface of the lead near the distal end of the lead. The plurality of electrodes includes a first set of segmented electrodes comprising at least two segmented electrodes disposed around a circumference of the lead at a first longitudinal position along the lead; and a second set of segmented electrodes comprising at least two segmented electrodes disposed around a circumference of the lead at a second longitudinal position along the lead. The device further includes one or more conductors that electrically couple together all of the segmented electrodes of the first set of segmented electrodes.

20 Claims, 12 Drawing Sheets

(56) References Cited

U.S. PATENT DOCUMENTS

| | | |
|---|---|---|
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 * | 4/2006 | Helland .................. 600/375 |
| 7,047,084 B2 | 5/2006 | Erickson et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,840,188 B2 | 11/2010 | Kurokawa |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,583,237 B2 | 11/2013 | Bedenbaugh |
| 2002/0156513 A1 | 10/2002 | Borkan |
| 2002/0183817 A1 | 12/2002 | Van Venrooij et al. |
| 2004/0098074 A1 | 5/2004 | Erickson et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0149335 A1 | 7/2006 | Meadows |
| 2006/0247697 A1 | 11/2006 | Sharma et al. |
| 2007/0203546 A1 | 8/2007 | Stone et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0269854 A1 | 10/2008 | Hegland et al. |
| 2009/0204192 A1 | 8/2009 | Carlton et al. |
| 2009/0204193 A1 | 8/2009 | Kokones et al. |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0125310 A1 | 5/2010 | Wilson et al. |
| 2010/0268298 A1 | 10/2010 | Moffitt et al. |
| 2011/0005069 A1 | 1/2011 | Pianca |
| 2011/0047795 A1 | 3/2011 | Turner et al. |
| 2011/0056076 A1 * | 3/2011 | Hegland et al. ................. 29/874 |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0313268 A1 | 12/2011 | Kokones et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0197424 A1 | 8/2013 | Bedenbaugh |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 7/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008038208 A2 | 4/2008 |
| WO | 2008053789 A1 | 5/2008 |
| WO | 2009025816 A1 | 2/2009 |
| WO | 2009102536 A1 | 8/2009 |

OTHER PUBLICATIONS

Response to Official Communication for U.S. Appl. No. 13/665,533, filed Oct. 30, 2013.
U.S. Appl. No. 13/906,776, filed May 31, 2013.
U.S. Appl. No. 13/951,057, filed Jul. 25, 2013.
International Search Report and Written Opinion for International Patent Application No. PCT/US2010/031442 mailed Aug. 25, 2010.
Official Communication for U.S. Appl. No. 12/761,622 mailed May 15, 2012.
Official Communication for U.S. Appl. No. 12/761,622 mailed Jan. 18, 2012.
U.S. Appl. No. 13/750,725, filed Jan. 25, 2013.
U.S. Appl. No. 13/787,171, filed Mar. 6, 2013.
U.S. Appl. No. 13/899,316, filed May 21, 2013.

* cited by examiner

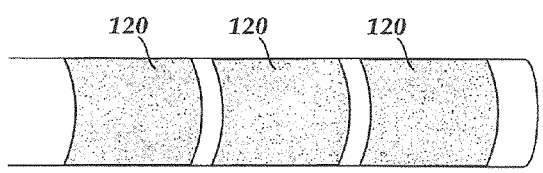 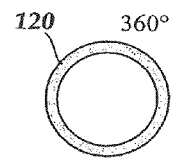 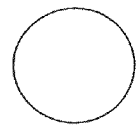
FIG. 7A　　　　　　FIG. 7B　　FIG. 7C
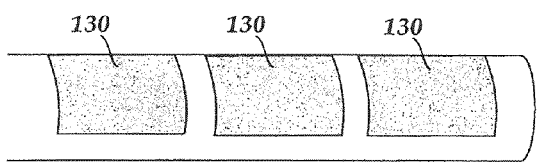 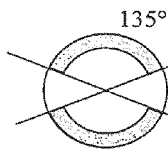 
FIG. 8A　　　　　　FIG. 8B　　FIG. 8C
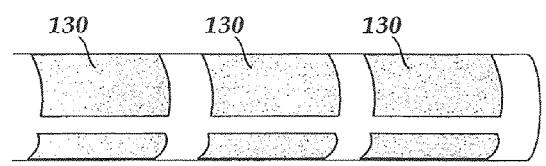 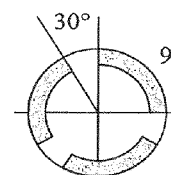 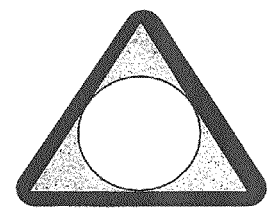
FIG. 9A　　　　　　FIG. 9B　　FIG. 9C

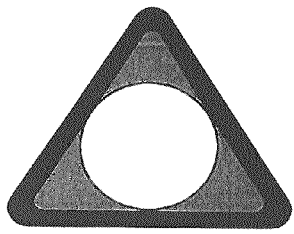
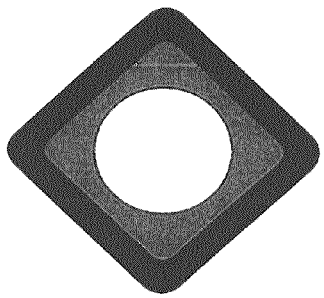
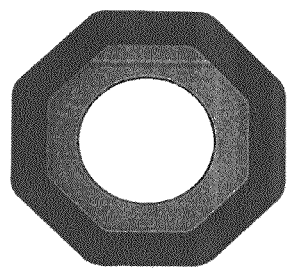
FIG. 10A          FIG. 10B          FIG. 10C
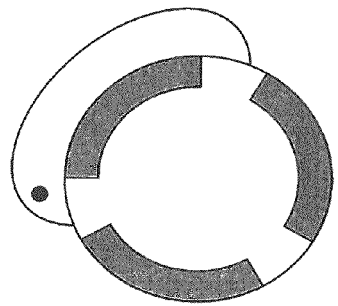
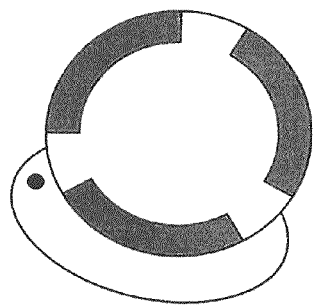
FIG. 11A                    FIG. 11B
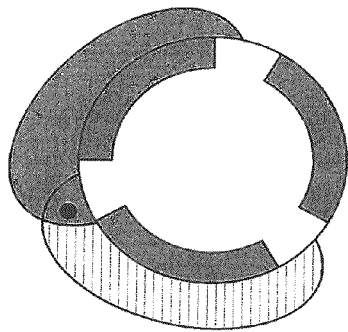
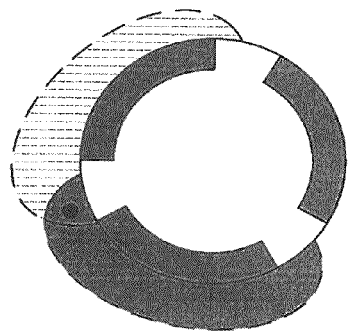
FIG. 11C                    FIG. 11D

DEEP BRAIN STIMULATION CURRENT STEERING WITH SPLIT ELECTRODES

CROSS REFERENCE TO RELATED APPLICATIONS

This application is a continuation of U.S. patent application Ser. No. 12/761,622 filed Apr. 16, 2010, now U.S. Pat. No. 8,473,061, issued Jun. 25, 2013, which claims the benefit of U.S. Provisional Patent Application Ser. No. 61/170,037 flied Apr. 16, 2009, and U.S. Provisional Patent Application Ser. No. 61/316,759 filed Mar. 23, 2010, all of which are incorporated herein by reference in their entirety.

FIELD

The invention is directed to devices and methods for brain stimulation including deep brain stimulation. In addition, the invention is directed to devices and method for brain stimulation using a lead having a plurality of segmented electrodes.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by electrodes, typically in the form of rings, disposed on the lead. The current projects from each electrode similarly and in all directions at any given length along the axis of the lead. Because of the shape of the electrodes, radial selectivity of the current is minimal. This results in the unwanted stimulation of neighboring neural tissue, undesired side effects and an increased duration of time for the proper therapeutic effect to be obtained.

BRIEF SUMMARY

One embodiment is a device for brain stimulation that includes a lead having a longitudinal surface, a proximal end, a distal end and a lead body. The device also includes a plurality of electrodes disposed along the longitudinal surface of the lead near the distal end of the lead. The plurality of electrodes includes a first set of segmented electrodes comprising at least two segmented electrodes disposed around a circumference of the lead at a first longitudinal position along the lead; and a second set of segmented electrodes comprising at least two segmented electrodes disposed around a circumference of the lead at a second longitudinal position along the lead. The device further includes one or more conductors that electrically couple together all of the segmented electrodes of the first set of segmented electrodes.

Another embodiment is a method for brain stimulation that includes inserting a device into a cranium of a patient. The device includes a lead having a longitudinal surface, a proximal end and a distal end, and a plurality of electrodes disposed along the longitudinal surface of the lead. The plurality of electrodes includes at least one set of segmented electrodes where each set of segmented electrodes has a plurality of segmented electrodes disposed around a circumference of the lead at a longitudinal position along the lead. The method further includes selectively producing anodic and cathodic currents at the plurality of electrodes to stimulate a target neuron using the plurality of electrodes. During operation, the anodic current or cathodic current is shifted from any one of the plurality of segmented electrodes to an adjacent one of the plurality of segmented electrodes.

Yet another embodiment is a method for brain stimulation that includes inserting a device into a cranium of a patient. The device includes a lead having a longitudinal surface, a proximal end and a distal end, and a plurality of electrodes disposed along the longitudinal surface of the lead. The plurality of electrodes includes at least one set of segmented electrodes where each set of segmented electrodes has a plurality of segmented electrodes disposed around a circumference of the lead at a longitudinal position along the lead. The method further includes selectively producing anodic and cathodic currents at the plurality of electrodes to stimulate a target neuron using the plurality of electrodes. A first timing channel is defined which provides a first set of stimulation pulses to any one of the plurality of segmented electrodes. At least one second timing channel is defined which provides at least a second set of stimulation pulses to any one of the plurality of segmented electrodes. The first and second sets of stimulation pulses are cycled with the first and second sets of stimulation pulses non-overlapping in the first and second timing channels.

A further embodiment is an implantable stimulation device for brain stimulation that includes a lead having a longitudinal surface, a proximal end and a distal end. The lead includes a plurality of electrodes disposed along the longitudinal surface of the lead near the distal end of the lead. The plurality of electrodes includes i) a first ring electrode disposed at a first longitudinal position along the lead, ii) a first set of segmented electrodes comprising at least three segmented electrodes disposed around a circumference of the lead at a second longitudinal position along the lead, iii) a second set of segmented electrodes comprising at least three segmented electrodes disposed around a circumference of the lead at a third longitudinal position along the lead, and iv) a second ring electrode disposed at a fourth longitudinal position along the lead. The second and third longitudinal positions are between the first and fourth longitudinal positions. The implantable stimulation device also includes a control unit coupleable to the lead. The implantable stimulation device is a constant-current, multi-channel device, with independent programmability of each stimulation channel to provide current steering.

In one embodiment, a device for brain stimulation includes a lead having a longitudinal surface, a proximal end and a distal end. A plurality of electrodes is disposed along the longitudinal surface of the lead near the distal end of the lead. The plurality of electrodes includes at least one ring electrode, and at least one set of segmented electrodes. Each set of segmented electrodes includes at least two segmented electrodes, which may be configured and arranged so as to collectively form a surface in the shape of a ring but having cutouts between them to separate the at least two segmented electrodes.

In another embodiment, a device for brain stimulation includes a lead having a longitudinal surface, a proximal end and a distal end. A plurality of electrodes is disposed along the longitudinal surface of the lead near the distal end of the lead. The plurality of electrodes includes at least one ring electrode, and at least one set of segmented electrodes. Each set of segmented electrodes includes a plurality of electrodes disposed at intervals around the circumference of the lead at or near a same longitudinal position along the lead.

In yet another embodiment, a method for brain stimulation includes inserting a device into a cranium of a patient. The device includes a lead having a longitudinal surface, a proximal end and a distal end. A plurality of electrodes is disposed along the longitudinal surface of the lead. The plurality of electrodes includes at least one ring electrode, and at least one set of segmented electrodes. The set of segmented electrodes includes at least two segmented electrodes that may be configured and arranged so as to collectively form a surface in the shape of a ring but having cutouts between them to separate the at least two segmented electrodes. Anodic and cathodic currents are selectively produced at the plurality of electrodes to stimulate a target neuron using the plurality of electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 7A is a schematic perspective view of one embodiment of a portion of a lead having a ring electrode, according to the invention;

FIG. 7B is a schematic cross-sectional view of the portion of the lead of FIG. 7A, according to the invention;

FIG. 7C is a schematic diagram of possible centroid locations of the monopolar and multipolar stimulation volume of the portion of the lead of FIG. 7A, according to the invention;

FIG. 8A is a schematic perspective view of one embodiment of a portion of a lead having sets of two segmented electrodes, according to the invention;

FIG. 8B is a schematic cross-sectional view of the portion of the lead of FIG. 8A, according to the invention;

FIG. 8C is a schematic diagram of possible centroid locations of the monopolar and multipolar stimulation volume of the portion of the lead of FIG. 8A, according to the invention;

FIG. 9A is a schematic view of one embodiment of a portion of a lead having sets of three segmented electrodes, according to the invention;

FIG. 9B is a schematic cross-sectional view of the portion of the lead of FIG. 9A, according to the invention;

FIG. 9C is a schematic diagram of possible centroid locations of the monopolar and multipolar stimulation volume of the lead of FIG. 9A, according to the invention;

FIG. 10A is a schematic diagram of possible centroid locations of the monopolar and multipolar stimulation volume of a lead having sets of three segmented electrodes, according to the invention;

FIG. 10B is a schematic diagram of the possible centroid locations of the monopolar and multipolar stimulation volume of a lead having sets of three segmented electrodes, according to the invention;

FIG. 10C is a schematic diagram of possible centroid locations of the monopolar and multipolar stimulation volume of a lead having sets of eight segmented electrodes, according to the invention;

FIG. 11A is a schematic diagram of one embodiment of an electrode stimulating a target, according to the invention;

FIG. 11B is a schematic diagram of a second embodiment of an electrode stimulating a target, according to the invention;

FIG. 11C is a schematic diagram of one embodiment of two electrodes simultaneously stimulating a target, according to the invention;

FIG. 11D is a schematic diagram of one embodiment of an electrode cycling technique, according to the invention;

DETAILED DESCRIPTION

The present invention is directed to the area of devices and methods for brain stimulation including deep brain stimulation. In addition, the invention is directed to devices and method for brain stimulation using a lead having a plurality of segmented electrodes.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Publication 2006/0149335 A1 ("Devices and Methods For Brain Stimulation"), and co-pending patent application U.S. Ser. No, 12/237,888 ("Leads With Non-Circular-Shaped Distal Ends For Brain Stimulation Systems and Methods of Making and Using"). Each of these references is incorporated herein by reference in its respective entirety.

Figure 12:
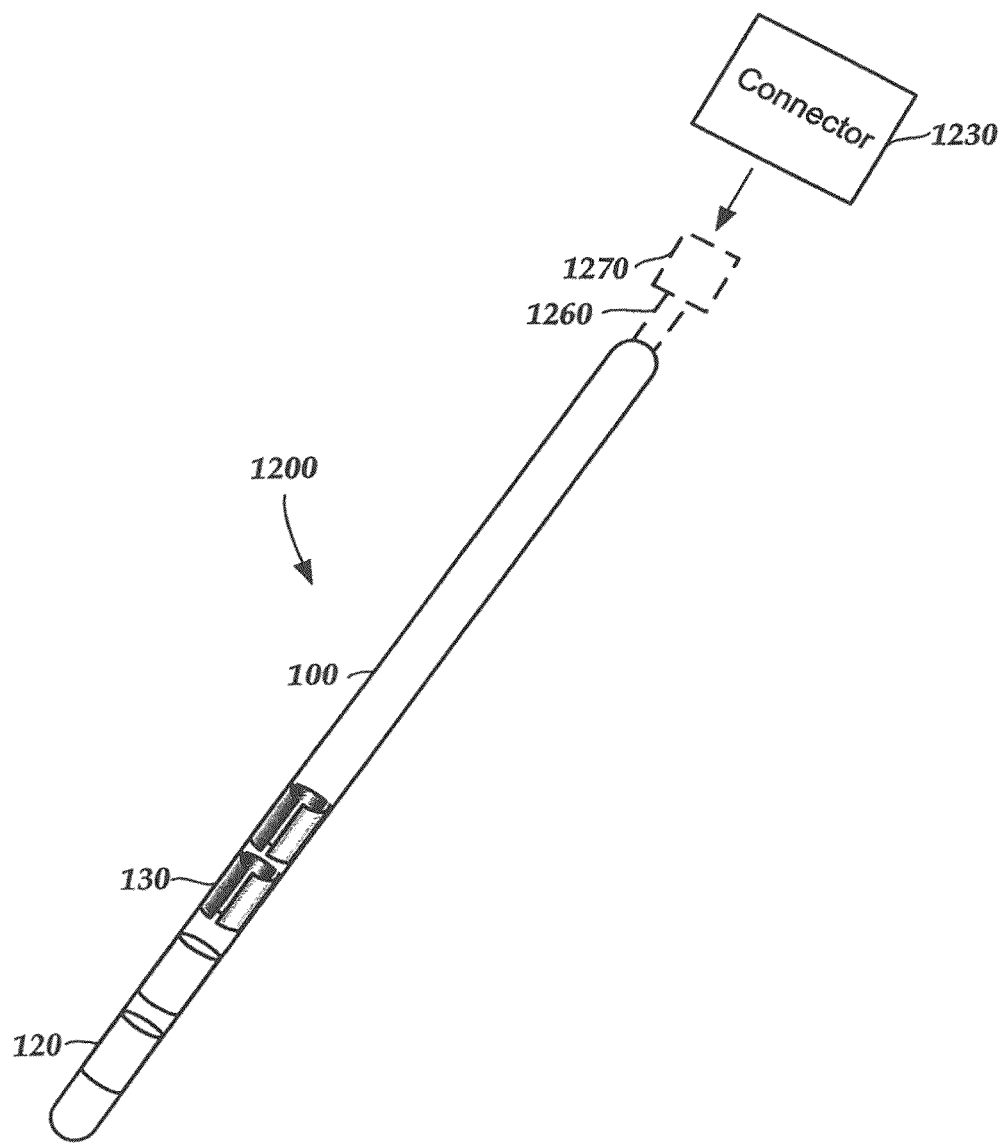
FIG. 12 is a schematic side view of one embodiment of a lead and a stylet, according to the invention.

FIG. 12 illustrates one embodiment of a device 1200 for brain stimulation. The device includes a lead 100, ring electrodes 120, segmented electrodes 130, a connector 1230 for connection of the electrodes to a control unit, and a stylet 1260 for assisting in insertion and positioning of the lead in the patient's brain. The stylet 1260 can be made of a rigid material. Examples of suitable materials include tungsten, stainless steel, or plastic. The stylet 1260 may have a handle 1270 to assist insertion into the lead, as well as rotation of the stylet and lead. The connector 1230 fits over the proximal end of the lead 100, preferably after removal of the stylet 1260.

In one example of operation, access to the desired position in the brain can be accomplished by drilling a hole in the patient's skull or cranium with a cranial drill (commonly referred to as a burr), and coagulating and incising the dura mater, or brain covering. The lead 100 can be inserted into the cranium and brain tissue with the assistance of the stylet 1260. The lead can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): rotate the lead, insert the lead, or retract the lead. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 100 for deep brain stimulation can include stimulation electrodes, recording electrodes, or both. In at least some embodiments, the lead is rotatable so that the stimulation electrodes can be aligned with the target neurons after the neurons have been located using the recording electrodes.

Stimulation electrodes may be disposed on the circumference of the lead to stimulate the target neurons. Stimulation electrodes may be ring-shaped so that current projects from each electrode equally in every direction at any given length along the axis of the lead. To enhance current steering, segmented electrodes can be utilized additionally or alternatively. Though the following description discusses stimulation electrodes, it will be understood that all configurations of the stimulation electrodes discussed may be utilized in arranging recording electrodes as well.

Figure 1:
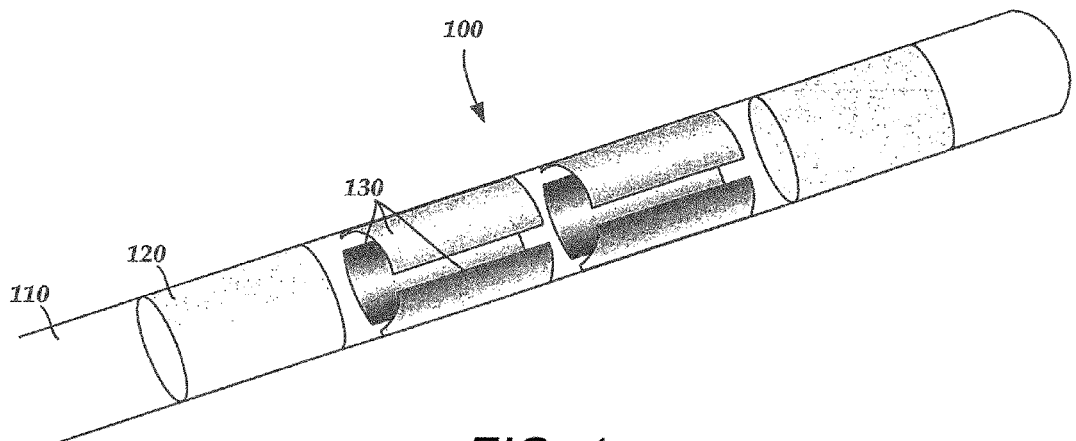
FIG. 1 is a schematic perspective view of one embodiment of a portion of a lead having a plurality of segmented electrodes, according to the invention.

FIG. 1 illustrates one embodiment of a lead 100 for brain stimulation. The device includes a lead body 110, one or more ring electrodes 120, and a plurality of segmented electrodes 130. The lead body 110 can be formed of a biocompatible, non-conducting material such as, for example, a polymeric material. Suitable polymeric materials include, but are not limited to, silicone, polyethylene, polyurethanes, polyureas, or polyurethane-ureas. In at least some instances, the lead may be in contact with body tissue for extended periods of time. In at least some embodiments, the lead has a cross-sectional diameter of no more than 1.5 mm and may be in the range of 0.75 to 1.5 mm in at least some embodiments, the lead has a length of at least 10 cm and the length of the lead may be in the range of 25 to 70 cm.

Stimulation electrodes may be disposed on the lead body 110. These stimulation electrodes may be made using a metal, alloy, conductive oxide, or any other suitable conductive material. Examples of suitable materials include, but are not limited to, platinum, iridium, platinum iridium alloy, stainless steel, titanium, or tungsten. Preferably, the stimulation electrodes are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a period of time and a cathode for a period of time. In other embodiments, the identity of a particular electrode or electrodes as an anode or cathode might be fixed.

Stimulation electrodes in the form of ring electrodes 120 may be disposed on any part of the lead body 110, usually near a distal end of the lead, FIG. 1 illustrates a portion of a lead having two ring electrodes. Any number of ring electrodes, or even a single ring electrode, may be disposed along the length of the lead body 110. For example, the lead body may have one ring electrode, two ring electrodes, three ring electrodes or four ring electrodes. In some embodiments, the lead will have five, six, seven or eight ring electrodes. It will be understood that any number of ring electrodes may be disposed along the length of the lead body 110. In some embodiments, the ring electrodes 120 are substantially cylindrical and wrap around the entire circumference of the lead body 110. In some embodiments, the outer diameter of the ring electrodes 120 is substantially equal to the outer diameter of the lead body 110. The width of ring electrodes 120 may vary according to the desired treatment and the location of the target neurons. In some embodiments the width of the ring electrode 120 is less than or equal to the diameter of the ring electrode 120. In other embodiments, the width of the ring electrode 120 is greater than the diameter of the ring electrode 120.

In at least some embodiments, the lead also contains a plurality of segmented electrodes 130. Any number of segmented electrodes 130 may be disposed on the lead body 110. In some embodiments, the segmented electrodes 130 are grouped in sets of segmented electrodes, each set disposed around the circumference of the lead at or near a particular longitudinal position. The lead may have any number of sets of segmented electrodes. In at least some embodiments, the lead has one, two, three, four, five, six, seven, or eight sets of segmented electrodes. In at least some embodiments, each set of segmented electrodes contains the same number of segmented electrodes 130. In some embodiments, each set of segmented electrodes contains three segmented electrodes 130. In at least some other embodiments, each set of segmented electrodes contains two, four, five, six, seven or eight segmented electrodes. The segmented electrodes 130 may vary in size and shape. In some embodiments, the segmented electrodes 130 are all of the same size, shape, diameter, width or area or any combination thereof. In some embodiments, the segmented electrodes of each set (or even all segmented electrodes) may be identical in size and shape.

In at least some embodiments, each set of segmented electrodes 130 may be disposed around the circumference of the lead body 110 to form a substantially or approximately cylindrical shape or ring around the lead body 110. The spacing of the segmented electrodes 130 around the circumference of the lead body 110 may vary as will be described with reference to FIGS. 7B, 8B and 9B. In at least some embodiments, equal spaces, gaps or cutouts are disposed between each segmented electrodes 130 around the circumference of the lead body 110. In other embodiments, the spaces, gaps or cutouts between segmented electrodes may differ in size or shape. In other embodiments, the spaces, gaps, or cutouts between segmented electrodes may be uniform for a particular set of segmented electrodes or for all sets of segmented electrodes. The segmented electrodes 130 may be positioned in irregular or regular intervals around the lead body 110.

Conductors (not shown) that attach to or from the ring electrodes 120 and segmented electrodes 130 also pass through the lead body 110. These conductors may pass through the material of the lead or through a lumen defined by the lead. The conductors are presented at a connector for coupling of the electrodes to a control unit (not shown), generally an multi-channel implantable pulse generator (IPG) having at least two independently controllable channels that deliver stimulus pulses that are programmable for current amplitude, pulsewidth and frequency of stimulus. Each channel is independently programmable so that one channel may act as a cathode and the other an anode in a bipolar stimulation mode, or only one channel acts as cathode while the housing of the IPG acts as an anode, or both channels deliver cathodic current while the housing of the implantable pulse generator acts as a return anode, or one channel may act as cathode while both the other channel and the housing of the IPG act as anode, or similar combinations of opposite polarity. More commonly the IPG can have 8, 16 or 32 independently programmable channels, wherein each channel can be independently (a) turned off, (b) be on as cathode or (c) be on as anode, at any one instant in time. Because each channel is fully independently functioning and programmable, there are many possible monopolar combinations (where the IPG housing is an anode electrode) and bipolar, multi-polar combinations (where the IPG housing is not an anode electrode). In an IP with four independently programmable channel a, b, c and d, each channel coupled separately four electrode segments of a segmented lead, there are the following monopolar combinations, a, b, c, d, ab, ac, ad, abc, abd, acd, bc, bd, cd, bcd, and abcd with the IPG housing as the anode. As one example, for abd, a possible programming is: a=1 milliamps current pulse, b=1.5 milliamps current pulse and c=1.25 current pulse, simultaneously delivered. The IPG housing sources 3.75 milliamps of current. When the IPG housing is off, then the possible combinations are ab, ac, ad, abc, abd, acd, bc, bd, cd, bcd, and abcd where at least one electrode in combination is functioning in one instant in time as an anode (−) return electrode and at least one electrode in the combination is functioning as a cathode (−). As an example, in the combination bcd, a possible way to program is: b=1 milliamps cathodic current, c=2.25 milliamps anodic current and d=1.25 milliamps cathodic current. Note that each channel can sink cathodic current or source anodic current, and each channel can have different amplitudes. This is what is meant by a multi-channel IPG having fully independently programmable, constant-current, channels. In one embodiment, the stimulation electrodes correspond to wire conductors that extend out of the lead body 110 and are then trimmed or ground down flush with the lead surface. The conductors may be coupled to a control unit to provide stimulation signals, often in the form of pulses, to the stimulation electrodes.

Figure 2:
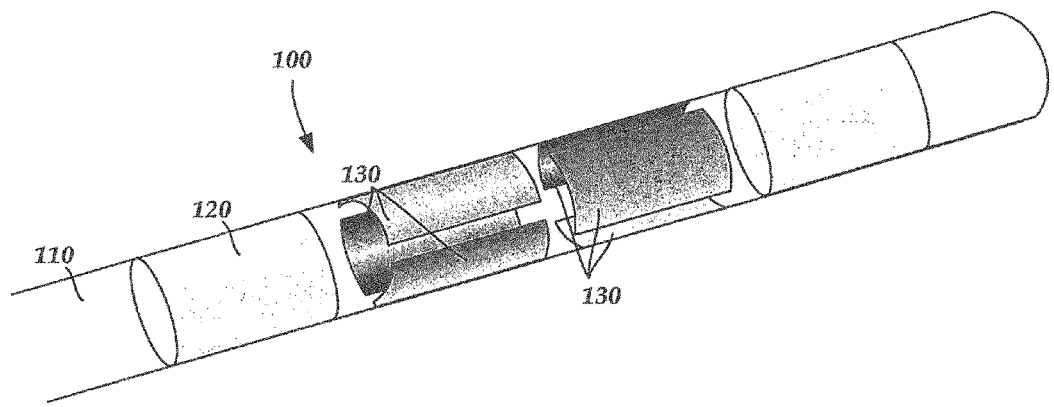
FIG. 2 is a schematic perspective view of another embodiment of a portion of a lead having a plurality of segmented electrodes arranged in a staggered orientation, according to the invention.

FIG. 2 is a schematic perspective view of another embodiment of a lead having a plurality of segmented electrodes. As seen in FIG. 2, the plurality of segmented electrodes 130 may be arranged in different orientations relative to each other. In contrast to FIG. 1, where the two sets of segmented electrodes are aligned along the length of the lead body 110, FIG. 2 displays another embodiment in which the two sets of segmented electrodes 130 are staggered. In at least some embodiments, the sets of segmented electrodes are staggered such that no segmented electrodes are aligned along the length of the lead body 110. In some embodiments, the segmented electrodes may be staggered so that at least one of the segmented electrodes is aligned with another segmented electrode of a different set, and the other segmented electrodes are not aligned.

Figure 3A:
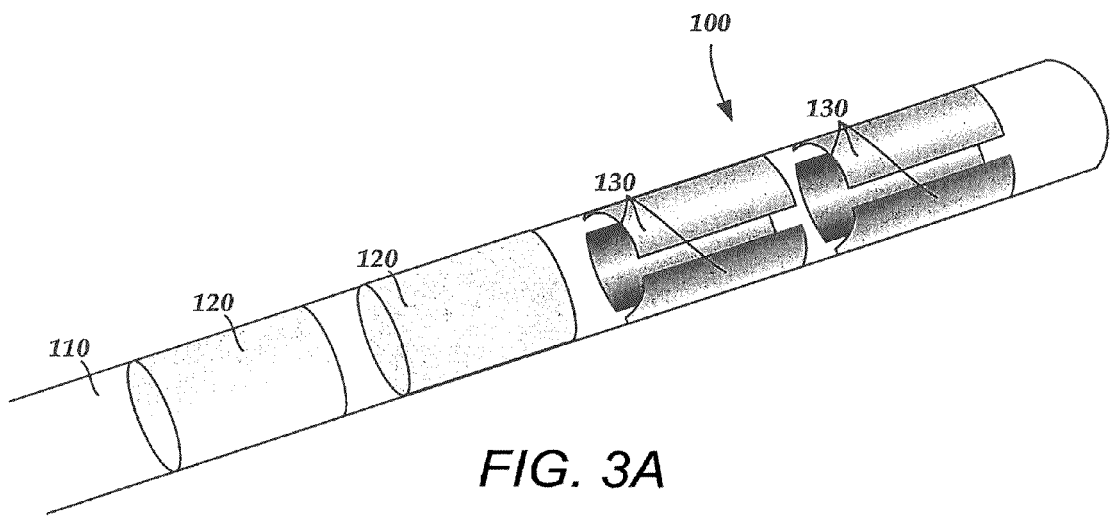
FIG. 3A is a schematic perspective view of a third embodiment of a portion of a lead having a plurality of segmented electrodes, according to the invention.
Figure 3B:
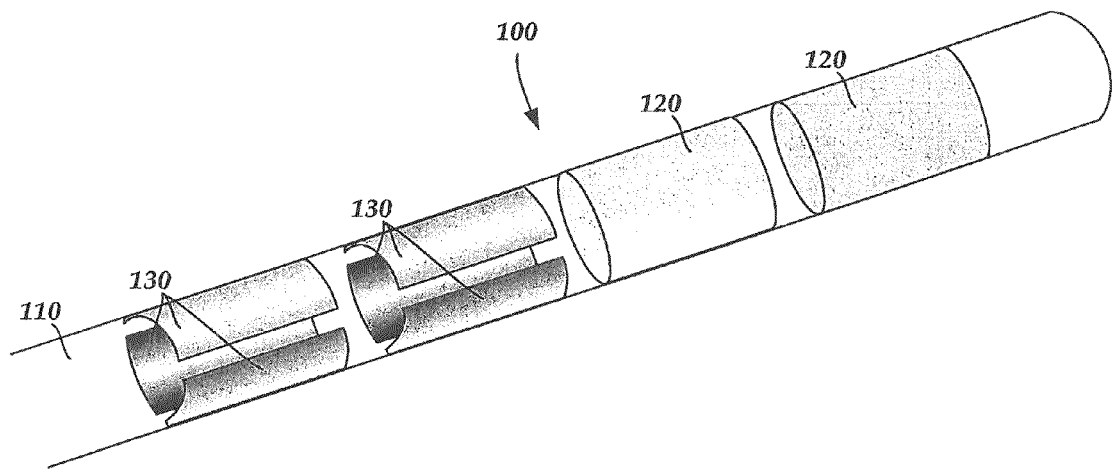
FIG. 3B is a schematic perspective view of a fourth embodiment of a portion of a lead having a plurality of segmented electrodes, according to the invention.

Any number of segmented electrodes 130 may be disposed on the lead body 110 in any number of sets. FIGS. 1 and 2 illustrate embodiments including two sets of segmented electrodes. These two sets of segmented electrodes 130 may be disposed in different configurations. FIG. 3A is a schematic perspective view of a third embodiment of a lead having a plurality of segmented electrodes. The lead body 110 of FIG. 3A has a proximal end and a distal end. As will be appreciated from FIG. 3A, the two sets of segmented electrodes 130 are disposed on the distal end of the lead body 110, distal to the two ring electrodes 120. FIG. 3B is a schematic perspective view of a fourth embodiment of a lead body 110. In FIG. 3B, the two sets of segmented electrodes 130 are disposed proximal to the two ring electrodes 120. By varying the location of the segmented electrodes 130, different coverage of the target neurons may be selected. For example, the electrode arrangement of FIG. 3A may be useful if the physician anticipates that the neural target will be closer to the distal tip of the lead body 110, while the electrode arrangement of FIG. 3B may be useful if the physician anticipates that the neural target will be closer to the proximal end of the lead body 110. In at least some embodiments, the ring electrodes 120 alternate with sets of segmented electrodes 130.

Any combination of ring electrodes 120 and segmented electrodes 130 may be disposed on the lead. In some embodiments the segmented electrodes are arranged in sets. For example, a lead may include a first ring electrode 120, two sets of segmented electrodes, each set formed of three segmented electrodes 130, and a final ring electrode 120 at the end of the lead. This configuration may simply be referred to as a 1-3-3-1 configuration. It may be useful to refer to the electrodes with this shorthand notation. Thus, the embodiment of FIG. 3A may be referred to as a 1-1-3-3 configuration, while the embodiment of FIG. 3B may be referred to as a 3-3-1-1 configuration. Other eight electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead will have 16 electrodes. Possible configurations for a 16-electrode lead include, but are not limited to 4-4-4-4, 8-8, 3-3-3-3-3-1 (and all rearrangements of this configuration), and 2-2-2-2-2-2-2-2.

Figure 4:
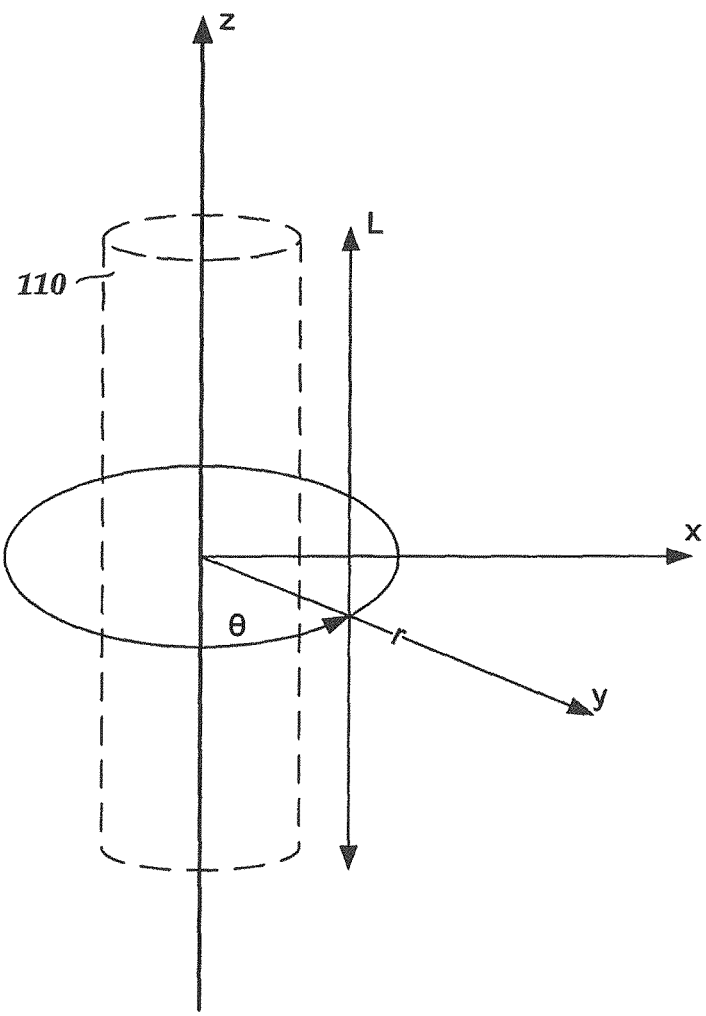
FIG. 4 is a schematic diagram of radial current steering along various electrode levels along the length of a lead, according to the invention.

FIG. 4 is a schematic diagram to illustrate radial current steering along various electrode levels along the length of a lead. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead body 110. In some embodiments, the radial distance, r, and the angle θ around the circumference of the lead body 110 may be dictated by the percentage of anodic current (recognizing that stimulation predominantly occurs near the cathode, although strong anodes may cause stimulation as well) introduced to each electrode as will be described in greater detail below. In at least some embodiments, the configuration of anodes and cathodes along the segmented electrodes 130 allows the centroid of stimulation to be shifted to a variety of different locations along the lead body 110.

As can be appreciated from FIG. 4, the centroid of stimulation can be shifted at each level along the length of the lead. The use of multiple sets of segmented electrodes 130 at different levels along the length of the lead allows for three-dimensional current steering. In some embodiments, the sets of segmented electrodes 130 are shifted collectively (i.e. the centroid of simulation is similar at each level along the length of the lead). In at least some other embodiments, each set of segmented electrodes 130 is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity. This concept will be further explained below with reference to FIGS. 8A-C and 9A-9C.

Figure 5:
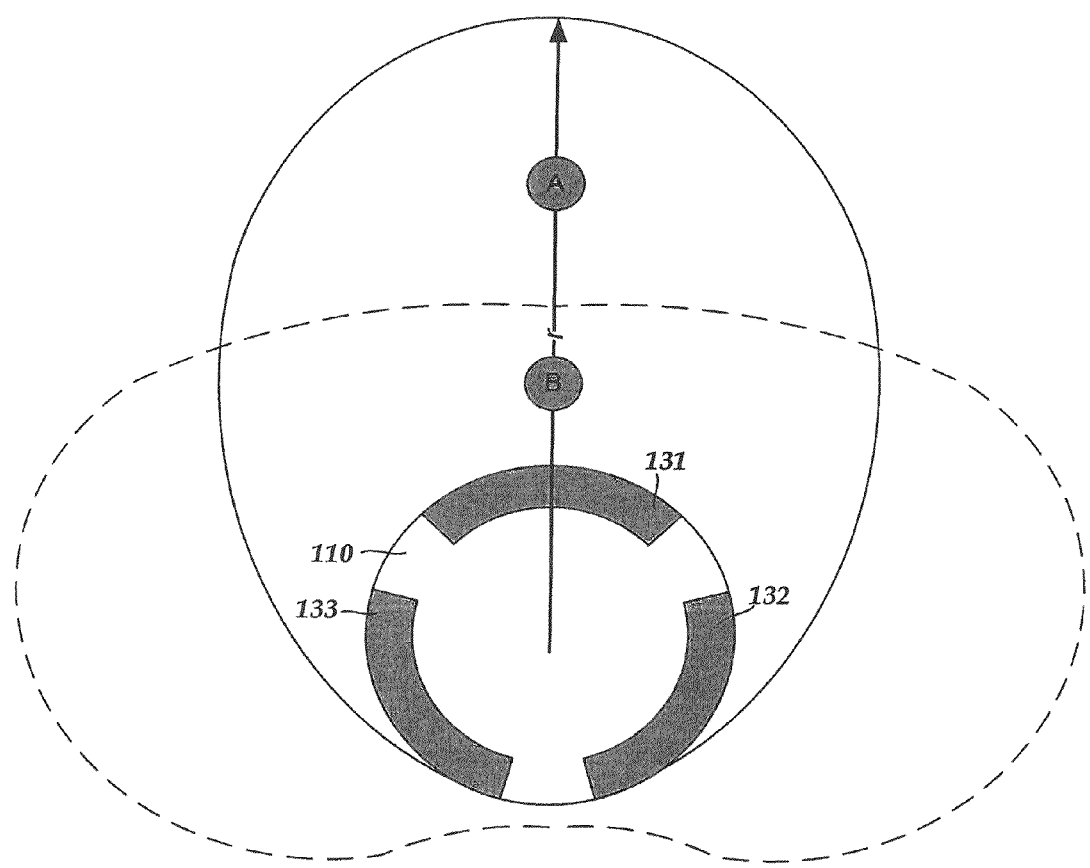
FIG. 5 is a schematic diagram of one embodiment of stimulation volume using monopolar and multipolar stimulation techniques, according to the invention.

Any type of stimulation technique can be used including monopolar stimulation techniques, bipolar stimulation techniques, and multipolar stimulation techniques. FIG. 5 is a schematic diagram of stimulation volume using monopolar and multipolar stimulation techniques. In monopolar stimulation techniques, all local electrodes are of the same polarity (i.e., an electrode of a different polarity is positioned far away, e.g., on the housing of the IPG, and does not substantially affect the stimulation field and centroid. Therefore, the stimulation centroid stays close to the stimulation electrode 131 as represented by B in FIG. 5. However, in multipolar stimulation, local anode(s) and cathode(s) are used. Therefore, the stimulation field is "driven away" from the electrodes, pushing out the stimulation centroid along the radius r. The centroid of the multipolar stimulation field is represented by A. Note that stimulation amplitude may need to be increased when switching from monopolar to multipolar to keep the same activation volume. As seen in FIG. 5, the stimulation volume varies between monopolar stimulation, represented by dashed lines, and multipolar stimulation, represented by solid lines. The centroid of the stimulation volume moves out along r when stimulation is changed from monopolar to muitipolar. In FIG. 5, the first segmented electrode 131 is used as the cathode and the second segmented electrodes 132 and 133 are used as anodes in the multipolar configuration, although any other configuration of anode and cathode is possible. Nerve fibers considered were perpendicular to the lead for the purpose of estimating the region of activation. It is recognized that cathodes, and more particularly anodes, may have a stimulating effect for other fiber orientations.

In at least some embodiments, the shift from monopolar stimulation to multipolar stimulation is incremental. For example, a device may start with a cathode (e.g. electrode 131) on the lead and 100% of the anode on the case of the device, or some other nonlocal location. The anode may then be incrementally moved to one or more of the local segmented electrodes 130. Any incremental shift can be used or the shift may even be continuous over a period of time. In some embodiments, the shift is performed in 10% increments. In some other embodiments, the shift is performed in 1%, 2%, 5%, 20%, 25%, or 50% increments. As the anode is incrementally moved from the case to one or more of the segmented electrodes 130, the centroid incrementally moves in the radial direction, r. Table A, below, illustrates an anode shift from a case to one segmented electrode at 10% increments:

TABLE A

| Electrode | Non-Local Anode |
|---|---|
| 0 | 100 |
| 10 | 90 |
| 20 | 80 |
| 30 | 70 |
| 40 | 60 |
| 50 | 50 |
| 60 | 40 |

TABLE A-continued

| Electrode | Non-Local Anode |
|---|---|
| 70 | 30 |
| 80 | 20 |
| 90 | 10 |
| 100 | 0 |

Similarly, Table B, below, illustrates an anodic shift from a non-local anode of the device to two segmented electrodes on the lead:

TABLE B

| Electrode 1 | Electrode 2 | Non-Local Anode |
|---|---|---|
| 0 | 0 | 100 |
| 10 | 10 | 80 |
| 20 | 20 | 60 |
| 30 | 30 | 40 |
| 40 | 40 | 20 |
| 50 | 50 | 0 |

In some embodiments, as in Table B, the two segmented electrodes equally split the anode. In other embodiments, the two segmented electrodes unequally split the anode. The two segmented electrodes may also split the anode in any ratio, such as 1.5:1, 2:1 or 3:1.

Figure 6:
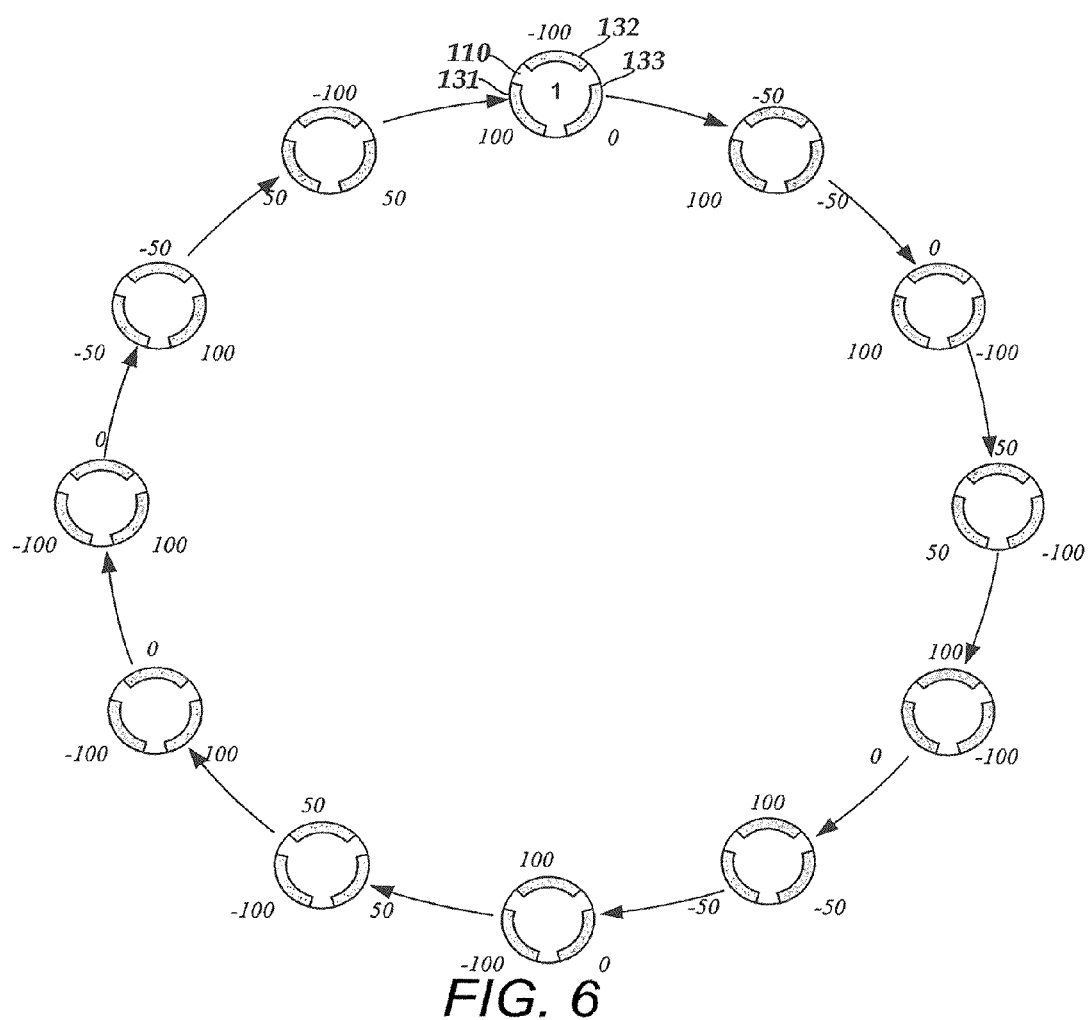
FIG. 6 is a schematic diagram of one embodiment of an anode and cathode current shifting technique, according to the invention.

Another stimulation technique is a method that can be called "chasing the cathode" and can be utilized to project the centroid of the stimulation volume. In this method, the anode chases the cathode around the circumference of the lead body 110 (i.e., as θ changes). It will be recognized that another embodiment can have the cathode chase the anode. After the cathodic current has incrementally shifted to the next segmented electrode, the anodic current begins to incrementally shift to another of the segmented electrodes, for a set of three segmented electrodes, the shift is to the previously cathodic segmented electrode. Once the anode has completely shifted, the present cathode begins to incrementally shift to the next segmented electrode, and the cycle continues. In at least some embodiments, three or more segmented electrodes are utilized for chasing the cathode. In some cases, the anode shifts may be larger (e.g., 20%) than the cathode shifts (e.g., 10%) or vice versa. FIG. 6 is a schematic diagram of the "chasing the cathode" technique. Each segmented electrode 131-133 of FIG. 6 is labeled with the relevant percentage of the local cathode, designated with (−), or local anode, designated with (+). For example, in the first step labeled "1", the first segmented electrode 130 is labeled 100, because that segmented electrode carries 100% of the local anode. Even if the 70% of the anode is on a the first segmented electrode 131 and 30% of the anode is on the case, the first segmented electrode 131 will be labeled as 100, because that electrode carries 100% of the local anode, even though it carries 70% of the system anode.

As seen in FIG. 6, the device begins with 100 on the first segmented electrode 131, −100 on the second segmented electrode 132 and 0 on the third segmented electrode 133. At a later point, the first segmented electrode 131 is shown at 100, the second segmented electrode 132 is shown at −50, and the third segmented electrode 133 is shown at −50. This incremental shift may be iterated until the device returns to the first state where the configuration is 100 on the first segmented electrode 131, −100 on the second segmented electrode 132 and 0 on the third segmented electrode 133. Table C, below, shows one cycle of the "current chasing" technique, where the anodic and cathodic shifts are performed at 10% increments.

TABLE C

| | Electrode 1 | Electrode 2 | Electrode 3 |
|---|---|---|---|
| 1. | 100 | −100 | 0 |
| 2. | 100 | −90 | −10 |
| 3. | 100 | −80 | −20 |
| 4. | 100 | −70 | −30 |
| 5. | 100 | −60 | −40 |
| 6. | 100 | −50 | −50 |
| 7. | 100 | −40 | −60 |
| 8. | 100 | −30 | −70 |
| 9. | 100 | −20 | −80 |
| 10. | 100 | −10 | −90 |
| 11. | 100 | 0 | −100 |
| 12. | 90 | 10 | −100 |
| 13. | 80 | 20 | −100 |
| 14. | 70 | 30 | −100 |
| 15. | 60 | 40 | −100 |
| 16. | 50 | 50 | −100 |
| 17. | 40 | 60 | −100 |
| 18. | 30 | 70 | −100 |
| 19. | 20 | 80 | −100 |
| 20. | 10 | 90 | −100 |
| 21. | 0 | 100 | −100 |
| 22. | −10 | 100 | −90 |
| 23. | −20 | 100 | −80 |
| 24. | −30 | 100 | −70 |
| 25. | −40 | 100 | −60 |
| 26. | −50 | 100 | −50 |
| 27. | −60 | 100 | −40 |
| 28. | −70 | 100 | −30 |
| 29. | −80 | 100 | −20 |
| 30. | −90 | 100 | −10 |
| 31. | −100 | 100 | 0 |
| 32. | −100 | 90 | 10 |
| 33. | −100 | 80 | 20 |
| 34. | −100 | 70 | 30 |
| 35. | −100 | 60 | 40 |
| 36. | −100 | 50 | 50 |
| 37. | −100 | 40 | 60 |
| 38. | −100 | 30 | 70 |
| 39. | −100 | 20 | 80 |
| 40. | −100 | 10 | 90 |
| 41. | −100 | 0 | 100 |
| 42. | −90 | −10 | 100 |
| 43. | −80 | −20 | 100 |
| 44. | −70 | −30 | 100 |
| 45. | −60 | −40 | 100 |
| 46. | −50 | −50 | 100 |
| 47. | −40 | −60 | 100 |
| 48. | −30 | −70 | 100 |
| 49. | −20 | −80 | 100 |
| 50. | −10 | −90 | 100 |
| 51. | 0 | −100 | 100 |
| 52. | 10 | −100 | 90 |
| 53. | 20 | −100 | 80 |
| 54. | 30 | −100 | 70 |
| 55. | 40 | −100 | 60 |
| 56. | 50 | −100 | 50 |
| 57. | 60 | −100 | 40 |
| 58. | 70 | −100 | 30 |
| 59. | 80 | −100 | 20 |
| 60. | 90 | −100 | 10 |
| 61. | 100 | −100 | 0 |

In some embodiments, the anode is located only on the case. In some other embodiments, the anode is partially located on the case and one or more electrodes. As previously indicated, the data in FIG. 6 and Table C indicates only the local percentages of the anode and the cathode. Thus, even though a segmented electrodes is labeled with 100, i.e. that it carries 100% of the local anode, it may carry anywhere between 1% to 100% of the total system anodic current. The same is true for cathodic current such that at any row, the local cathodic current may be anywhere between 1% to 100% of the system cathodic current, even though it is labeled as 100.

A multi-channel set up technique may also be used to shift current from one electrode to another. For example, the use of two timing channels allows two potentially-viable sets of stimulation parameters to be applied to the patient during set up in an interleaved fashion. So applied, the patient will independently feel the effects of the settings of both timing channels, but in a manner that does not blur the effect of two. Thus, field shifting in this manner may reduce or eliminate intermediate states that reduce the efficacy of the therapy.

This type of field shifting will be referred to as interleaved field shifting and will be described with reference to Table D, below:

TABLE D

|  | Electrode 1 | Electrode 2 | Electrode 3 | Electrode 4 |
|---|---|---|---|---|
| Channel A | 50 | −100 | 50 | 0 |
| Channel B | 0 | 0 | 0 | 0 |
|  |  | Step 1 |  |  |
| Channel A | 50 | −100 | 50 | 0 |
| Channel B | 0 | 25 | −50 | 25 |
|  |  | Step 2 |  |  |
| Channel A | 50 | −100 | 50 | 0 |
| Channel B | 0 | 50 | −100 | 50 |
|  |  | Step 3 |  |  |
| Channel A | 50 | −100 | 50 | 0 |
| Channel B | 0 | 50 | −100 | 50 |
|  |  | Step 4 |  |  |
| Channel A | 25 | −50 | 25 | 0 |
| Channel B | 0 | 50 | −100 | 50 |

As shown in Table D, two channels, Channel A and Channel B, are used to shift the current. In timing Channel A, the initial conditions of electrodes 1-4 are 50% on the first, −100% on the second, and 50% on the third. There is no current on the fourth electrode in timing Channel A at this initial condition. However, if the user desires to shift current to the fourth electrode then two timing channels may be used to accomplish this task. The user may begin by using a controller to shift current to timing Channel B.

Thus, in a first step the current associated with timing Channel A will remain constant, while timing Channel B will shift to a state having 25% on the second electrode, −50% on the third electrode and 25% on the fourth electrode. Notice that at this first step, establishment of current in timing Channel B does not immediately affect the amount of current in the initial conditions of timing Channel A as described in the embodiment of Table C.

In a second step, the current directed to timing Channel B may again be increased by the same amount, although the shifts need not be incremental. As can be appreciated from Table D, after the second step, the current in timing Channel B now matches that of timing Channel A, but is shifted over by one electrode. Subsequent steps are then applied to incrementally remove the current from the initial condition electrodes in timing Channel A, which eventually leaves as active only the final condition electrodes in timing Channel B. At this point, timing Channel B is the only currently active timing channel with segmented electrodes 2-4 having the state of the initial segmented electrodes 1-3.

As can be appreciated from Table D, movement from the initial conditions to the final conditions is accomplished without the intermediary steps during which the electrodes are really not indicative of either the initial or final conditions. Thus, useful stimulation may be optimized and unnecessary side effects reduced.

FIG. 7A is a schematic view of a lead having ring electrodes 120. The ring electrodes 120 completely encircle the circumference of the lead body 110. FIG. 7B is a schematic cross-sectional view of the lead of FIG. 7A, showing the ring electrodes 120 encircling the lead body 110. Any number of ring electrodes 120 may be disposed on the lead body 110. In some embodiments, where only ring electrodes 120 are disposed on the lead body 110, the centroid of stimulation can only be located at a single point within a specified plane normal to L, the length of the lead, as illustrated in FIG. 7C.

FIG. 8A is a schematic view of the lead having three sets of segmented electrodes, each set having two segmented electrodes 130. As illustrated in FIG. 8B, in some embodiments, two 45° cutouts are formed between the two segmented electrodes 130, with each segmented electrode 130 being formed of a 135° segment. It will be recognized that the size and shape of the segmented electrodes and cutouts can be varied. The two segmented electrodes 130 may be formed to cover any portion of the lead and the cutouts may be arranged to be of any distance. For example, each segmented electrode 130 may be formed of a 75°, 90° or 120° segment. In some embodiments, each cutout is of the same size. In other embodiments, the two cutouts are of different sizes. By adding an additional electrode, or electrode segment, multipolar stimulation techniques are possible. FIG. 8C is a schematic representation of the monopolar and multipolar stimulation of the lead of FIG. 8A. As seen in FIG. 8C, the centroid of the monopolar stimulation of the two electrode segments is a straight line within a specified plane normal to L. In embodiments utilizing multipolar stimulation, the centroid of stimulation may be located similar to that of monopolar stimulation but with an increased range, due to the anode driving out the centroid.

FIG. 9A is a schematic view of a lead having three sets of segmented electrodes, each circumferential set having three segmented electrodes 130. It will be recognized that the size and shape of the segmented electrodes and cutouts (or space between the segmented electrodes in the circumferential set) can be varied. As described above, each of the three segmented electrodes 130 may be formed of segments of different lengths. As illustrated in FIG. 9B, the segmented electrodes of FIG. 9A may be formed of 90° segments, separated by 30° cutouts or gaps. In some other embodiments, the segments cover only 45°, 60° or 75°. In at least some embodiments, the cutouts (or space between segments in a set) are of different lengths. FIG. 9C is a schematic representation of the monopolar and multipolar stimulation of the lead of FIG. 9A. As seen in FIG. 9C, the addition of a third segmented electrode greatly increases the possibilities for stimulation. With a set of three segmented electrodes 130 and using only monopolar stimulation, the centroid of stimulation may be located anywhere in a triangular space within a specified plane normal to L, the length of the lead. With multipolar stimulation, the centroid of stimulation may be located in an increased range within a triangular space within a specified plane normal to L. Thus, multipolar stimulation may be used in all embodiments having more than two segmented electrodes 130 to drive out the centroid and allow for extended stimulation coverage. Because each electrode segment may be independently programmed for different current amplitude and, furthermore, as cathode, anode or off, at any instant in time, the stimulation field can be tremendously varied around the circumference and length L of the lead. Independent current control of each stimulation channel permits radial current steering, (i.e., where at least two electrodes, placed closely together, deliver simultaneous stimulus pulses, having same or different current amplitudes, and effectively place the centroid of stimulus at an angular position between the two electrodes.) The same principle applies with three or more electrodes that deliver independent constant current stimulus pulses. In, effect, it permits the creation of virtual electrodes between two real electrodes or complex stimulus current gradients around three or more electrodes. This is known as "current steering".

FIGS. 10A, 10B, and 10C are schematic representations of the monopolar and multipolar stimulation of a lead using three, four and eight segmented electrodes. A comparison between the stimulation for monopolar and multipolar stimulation may be appreciated with reference to FIGS. 10A 10B, and 10C. For example, as previously described, when three segmented electrodes are disposed around the circumference of the lead, the centroid of stimulation may be located anywhere in a triangular space within a specified plane normal to L, the length of the lead. Embodiments utilizing multipolar stimulation techniques using these same segmented electrodes allow for extended stimulation coverage and projecting of the centroid of stimulation.

FIG. 10B illustrates the monopolar and multipolar stimulation of a lead having four segmented electrodes. With four segmented electrodes at each level, an 8-electrode lead design may be formed. In at least some embodiments, four segmented electrodes are disposed on a lead having two other sets of segmented electrodes, each set having two segmented electrodes. With four segmented electrodes, the centroid of stimulation may be located anywhere in a square space within a specified plane normal to L, the length of the lead. As with the three segmented electrode configuration, a multipolar configuration can project the centroid so that the centroid of stimulation may be located anywhere in a larger square space within a specified plane normal to L.

FIG. 10C illustrates the monopolar and multipolar stimulation of a lead having eight segmented electrodes at a given level. With eight segmented electrodes at each level, a 16-electrode lead design may be formed. In at least some embodiments, eight segmented electrodes are disposed on a lead having any other number of segmented electrodes. For example, in some embodiments, the lead will have eight segmented electrodes at one level, and two other sets of four segmented electrodes, one at each level. As seen in FIG. 10C, with eight segmented electrodes, the centroid of stimulation may be located anywhere in an octagonal steering space within a specified plane normal to L, the length of the lead. As with other configurations, a multipolar configuration will drive out the centroid so that the centroid of stimulation may be located anywhere in a larger octagonal steering space within a specified plane normal to L.

In some embodiments, the device may be coupled to an implantable pulse generator. The implantable pulse generator may contain multiple current sources. For example, the implantable pulse generator may contain a distinct current source for each stimulation electrode. In some embodiments, the implantable pulse generator contains multiple voltage sources.

In at least some embodiments, a cycling technique may also be used to program the device with greater specificity. The cycling technique may include, for example, repeatedly shifting the stimulation from one area to another. Each area may define a set of stimulation parameters, including but not limited to one or more of electrode configuration, amplitude, pulse width, or current distribution. Cycling techniques may be used to expand the total area of stimulation by, for example, placing the centroid of stimulation effectively somewhere between the position of the two electrodes by rapidly alternating or cycling between each of two electrodes.

For example, suppose there are two electrodes A and B. Electrode A delivers pulses of 1.5 milliamps whereas Electrode B delivers 1.1 milliamps. The delivery of the stimulus pulses are rapidly alternated between Electrode A and Electrode B, doubling the frequency of stimulus in the overlap area, effectively emulating a virtual electrode between Electrodes A and B. The virtual electrode is positioned closer to Electrode B. This rapid cycling is yet another way to achieve a region of high rate stimulation between two electrodes. To effect such rapid cycling, the IPG must be capable of rapidly cycling between stimulation channels, or stimulate out of phase between stimulation channels. Or, if the electrodes are placed far enough away from each other, and the current fields do not substantially overlap, the two electrodes can be used to stimulate two targets pseudo-simultaneously. Cycling techniques may also be used to eliminate stimulation of unwanted neural tissue, reduce side effects, and give the user increased programming specificity.

Cycling techniques used for eliminating stimulation of unwanted neural tissue will be discussed with respect to FIGS. 11A-11D. In at least some embodiments, stimulation produces a therapeutic effect at frequencies above 130 Hz. Therefore, target areas are often stimulated with pulses above 130 Hz. However, often more neural tissue is stimulated than necessary. As shown in FIGS. 11A and 11B, the target, denoted by a black dot, is located between two of the segmented electrodes. Using either segmented electrode effectively stimulates the target as shown in FIGS. 11A and 11B. However, as evident from these figures, a large amount of unnecessary tissue may be stimulated. FIG. 11C illustrates a method in which both segmented electrodes are employed to stimulate the target. When both electrodes are used, the target is still effectively stimulated, but an increased area of neural tissue is unnecessarily stimulated. FIG. 11D illustrates a method in which both segmented electrodes are employed to stimulate the target, each segmented electrode stimulating at only half the original frequency. In embodiments where each segmented electrode intermittently stimulates with half the original frequency, the overlapping area is stimulated with the original frequency. Thus, the overlapping area may be effectively stimulated at therapeutic frequencies and the non-overlapping areas, the area enclosed within a dashed line, are not stimulated at the therapeutic frequency because they are stimulated at a reduced frequency. Thus, in some embodiments, the cycling technique may be used to refine the area of tissue stimulated at a therapeutic frequency.

The introduction of a plurality of segmented electrodes may also be used with a technique which can be called "search light" programming. In some embodiments, the stimulation volume may act like the beam of light from a lighthouse. The "beam" of electrical stimulation may be swept around the lead similar to how a beam of light is swept around a lighthouse or search light. Because multiple levels of electrodes are introduced along the length of the lead, the beam of electrical stimulation may also move up and down along the lead axis in addition to rotating around the circumference of the lead.

The system may utilize various electrodes and the methods described above, such as cathode and anode shifting to swing the beam or electrical activation around and up and down the longitudinal axis of the lead. In some embodiments, sweeping the beam of electrical stimulation aids in optimizing therapeutic benefits, in some other embodiments, the sweeping of the electrical stimulation is useful in selecting programs of stimulation parameters. In some embodiments, the physician may swing the beam of electrical stimulation to one area, then another, and then another to optimize the therapy and/or to determine the best target. In some other embodiments, the physician may program the system to swing back and forth between two or more targets or areas in a cyclical manner. In at least some other embodiments, the patient may swing the beam of electrical stimulation around until their symptoms are reduced and/or until therapy is complete. In yet another example, a computer system may collect various inputs while automatically sweeping the beam of electrical activation to optimize the therapy and/or to determine the best target.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Figure 13:
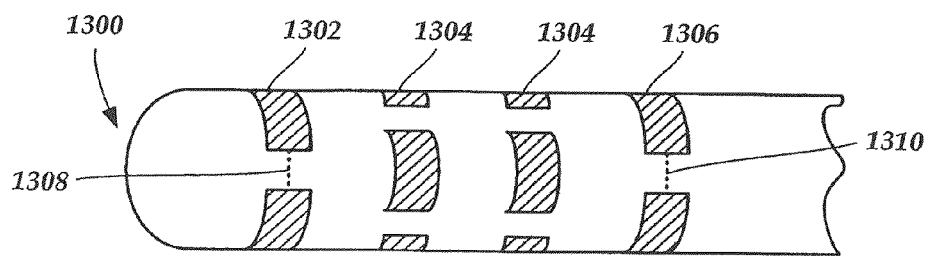
FIG. 13 is a schematic side view of a portion of an embodiment of a lead with segmented electrodes including ganged (i.e., electrically coupled) segmented electrodes, according to the invention.

There are many additional electrode arrangements that can be devised. FIG. 13 is a schematic side view of a distal end of one embodiment of a lead 1300 with, starting from the distal end of the lead, a group of two segmented electrodes 1302, two groups of three segmented electrodes 1304 each, and another group of two segmented electrodes 1306. In this embodiment, the group of two segmented electrodes 1302 are ganged together (i.e., electrically coupled together) as schematically indicated by line 1308. In addition, the group of two segmented electrodes 1306 are also ganged together as schematically indicated by line 1310.

Figure 14:
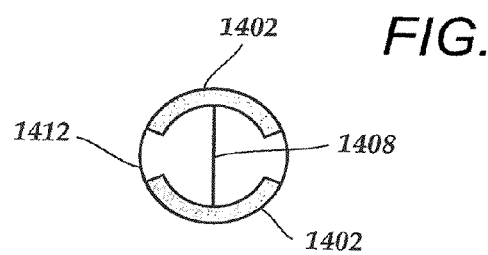
FIG. 14 is a schematic cross-sectional view of a portion of an embodiment of a lead with ganged (i.e., electrically coupled) electrodes, according to the invention.
Figure 15:
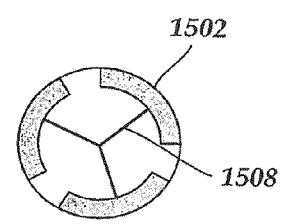
FIG. 15 is a schematic cross-sectional view of a portion of another embodiment of a lead with ganged (i.e., electrically coupled) electrodes, according to the invention.

FIG. 14 schematically illustrates one arrangement for ganging two electrodes together which includes coupling the two electrodes 1402 using a conductor 1408 that passes through the lead body 1412. This conductor 1408 can be coupled to a conductor (not shown) that passes through the lead body to the proximal end of the lead to provide for connection to the control unit. Alternatively, one of the electrodes 1402 is electrically coupled to a conductor (not shown) that passes through the lead body to the proximal end of the lead to provide for connection to the control unit or implantable pulse generator (IPG) with independently controllable, constant-current stimulation channels and the other electrode is coupled to the first electrode by the conductor 1408. FIG. 15 schematically illustrates a similar arrangement for electrically coupling three electrodes 1502 using conductors 1508.

Figure 16:
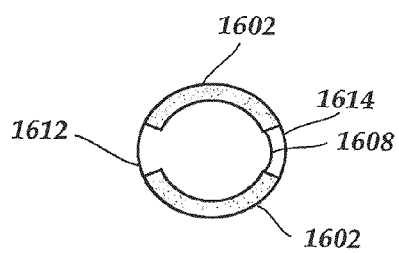
FIG. 16 is a schematic cross-sectional view of a portion of a further embodiment of a lead with ganged (i.e., electrically coupled) electrodes, according to the invention.
Figure 17:
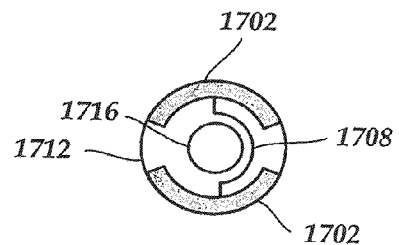
FIG. 17 is a schematic cross-sectional view of a portion of yet another embodiment of a lead with ganged (i.e., electrically coupled) electrodes, according to the invention.

FIG. 16 schematically illustrates another arrangement of two segmented electrodes 1602 that are coupled by a conductor 1608 that is covered by insulating material 1614 that is preferably part of, or becomes part of, the lead body 1612. This conductor 1608 might be a wire or may be a thin, flat conductor or some other connecting conductor. FIG. 17 schematically illustrates yet another arrangement with two electrodes 1702 and a conductor 1708. In this particular arrangement, the lead body 1712 defines a lumen 1716 (e.g., a stylet lumen) and the conductor is 1708 arranged around the lumen.

Figure 18:
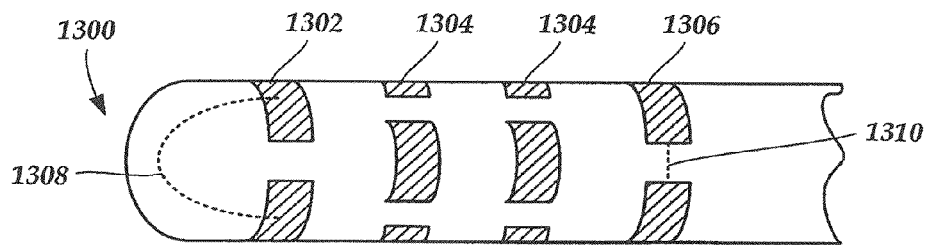
FIG. 18 is a schematic side view of a portion of another embodiment of a lead with segmented electrodes including ganged (i.e., electrically coupled) segmented electrodes, according to the invention.

FIG. 18 schematically illustrates yet another arrangement, using the same reference numerals as the embodiment of FIG. 13, in which the conductor 1308 is arranged in a path directed toward a tip of the lead 1300. This may be particularly useful to avoid a lumen (e.g., a stylet lumen) that passes through a portion of the lead, but is not present at the distal end of the lead. In alternative embodiments, separate conductors may be electrically coupled to each electrode and then the separate conductors are both electrically coupled to another conductor that passes through the lead body to the proximal end of the lead to provide for connection to the control unit (for example, an IPG, with independent controllable, constant-current stimulation channels).

Figure 19:
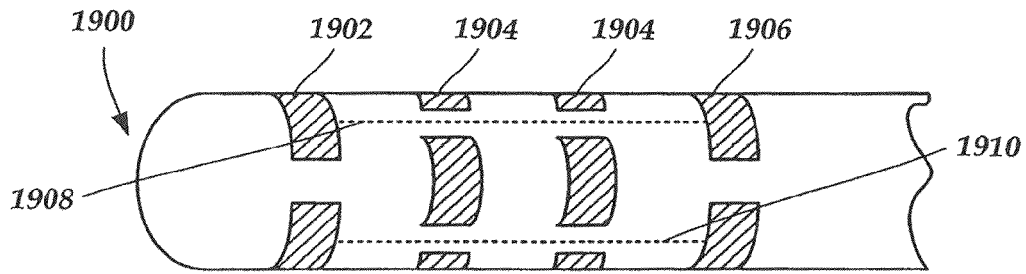
FIG. 19 is a schematic side view of a portion of a further embodiment of a lead with segmented electrodes including ganged (i.e., electrically coupled) segmented electrodes, according to the invention.

FIG. 19 schematically illustrates yet another embodiment of a lead 1900 with, starting from the distal end of the lead, a group of two segmented electrodes 1902, two groups of three segmented electrodes 1904 each, and another group of two segmented electrodes 1906. In this arrangement, each of the electrodes 1902 is ganged with one of the electrodes 1906 as schematically illustrated by the lines 1908 and 1910. It will be recognized that it is also possible to gang more than one of the electrodes 1902 with one or more of the electrodes 1906 or vice versa.

Figure 20:
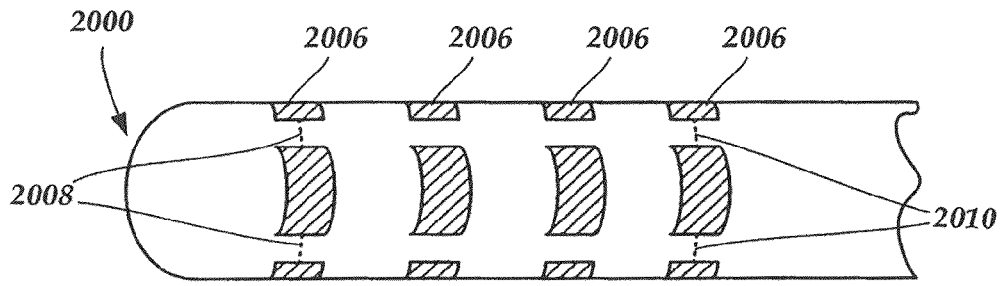
FIG. 20 is a schematic side view of a portion of yet another embodiment of a lead with segmented electrodes including ganged (i.e., electrically coupled) segmented electrodes, according to the invention.
Figure 29:
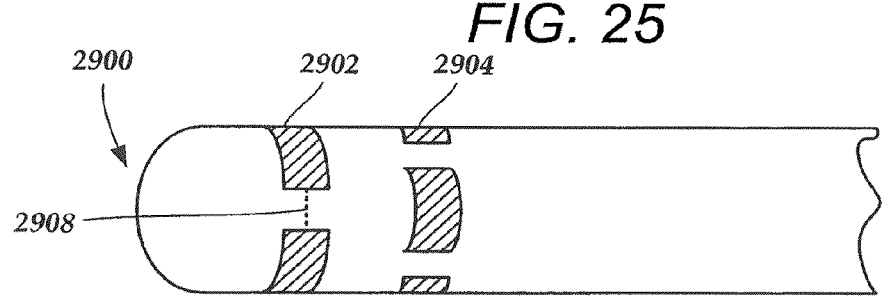
FIG. 29 is a schematic side view of a portion of a further embodiment of a lead with segmented electrodes including ganged (i.e., electrically coupled) segmented electrodes, according to the invention.

FIG. 29 schematically illustrates another embodiment of a lead 2900. In this instance, there is one circumferential group of two segmented electrodes 2902 ganged together and a second circumferential group of three segmented electrodes 2904. FIG. 20 schematically illustrates yet another embodiment of a lead 2000. In this instance, there are four groups of three segmented electrodes 2006 each. In the illustrated embodiment, the distal group 2006 (on the left) and the most proximal group 2006 (on the right) are ganged together as schematically indicated by lines 2008, 2010, respectively. It will be understood that in each of the embodiments described herein the order of the groups and which group(s) of electrodes are ganged together can be changed to form any possible arrangement.

Figure 21:
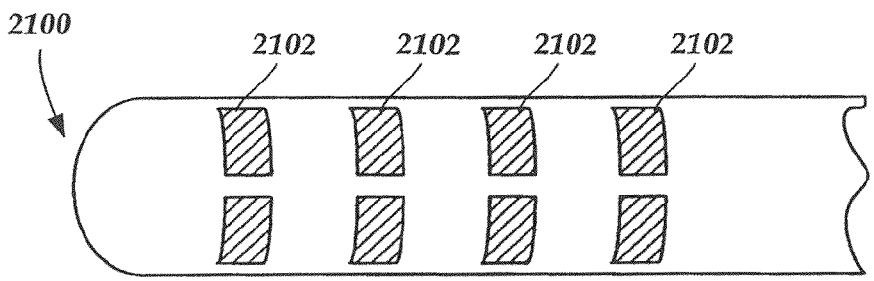
FIG. 21 is a schematic side view of a portion of an embodiment of a lead with segmented electrodes, according to the invention.
Figure 22:
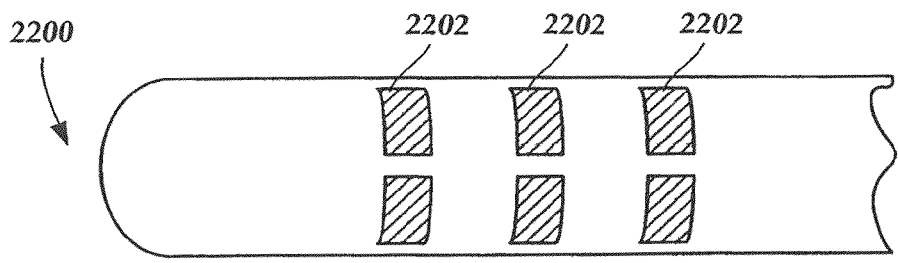
FIG. 22 is a schematic side view of a portion of another embodiment of a lead with segmented electrodes, according to the invention.
Figure 23:
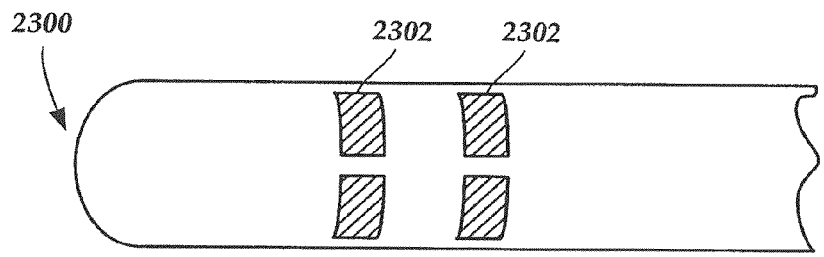
FIG. 23 is a schematic side view of a portion of a further embodiment of a lead with segmented electrodes, according to the invention.

Leads can be prepared with only segmented electrodes that are not ganged together. FIG. 21 schematically illustrates an embodiment of a lead 2100 with four groups of segmented electrodes 2102. Each circumferential group of segmented electrodes includes four electrodes. Thus, the total number of electrodes on lead 2100 is sixteen. FIG. 22 schematically illustrates an embodiment of a lead 2200 with three groups of segmented electrodes 2202. Each group of segmented electrodes includes four electrodes. Thus, the total number of electrodes on lead 2200 is twelve. FIG. 23 schematically illustrates an embodiment of a lead 2300 with three groups of segmented electrodes 2302. Each group of segmented electrodes includes four electrodes. Thus, the total number of electrodes on lead 2300 is eight. It will be understood that other leads can be made with different numbers of groups (e.g., two, three, four, five, six, or more groups) and different numbers of segmented electrodes in each group (e.g., two, three, four, five, six, or more electrodes). It will also be understood that the number of electrodes in each circumferential group may be the same or may be different. In some embodiments, the lead does not include a ring electrode. In some embodiments, the lead does not include segmented electrodes that are ganged together.

Figure 24:
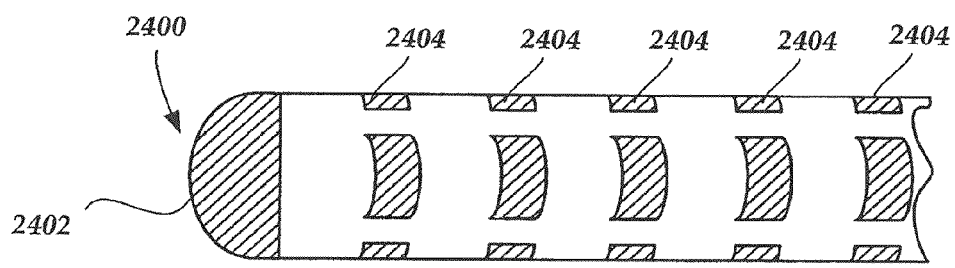
FIG. 24 is a schematic side view of a portion of an embodiment of a lead with segmented electrodes and a tip electrode, according to the invention.
Figure 25:
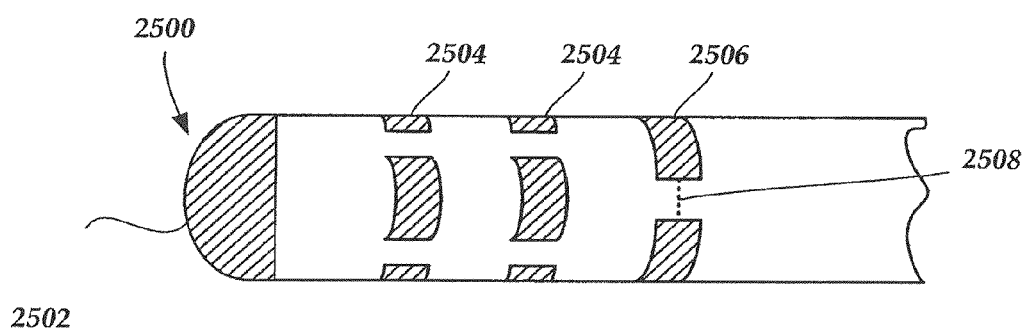
FIG. 25 is a schematic side view of a portion of another embodiment of a lead with segmented electrodes and a tip electrode, according to the invention.

Leads can also include a tip electrode, FIG. 24 schematically illustrates one embodiment of a lead 2400 with a tip electrode 2402 and five groups of segmented electrodes 2404 with three segmented electrodes per group. FIG. 25 schematically illustrates one embodiment of lead 2500 with a tip electrode 2502, two groups of segmented electrodes 2504 with three segmented electrodes per group, and a group of two segmented electrodes 2506 that are ganged together as schematically illustrated by the line 2508. It will be recognized that other arrangements with differing numbers of groups and numbers of electrodes in the groups can be presented. The embodiment of FIG. 25 includes both a tip electrode and a group of ganged segmented electrodes. It will be recognized that a tip electrode can be added to any of the other embodiments disclosed herein.

Figure 26:
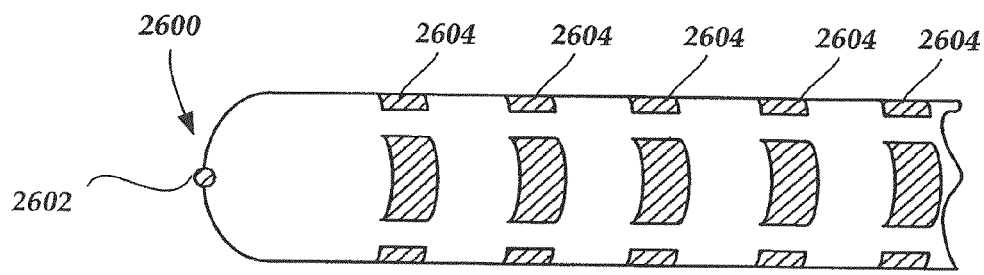
FIG. 26 is a schematic side view of a portion of an embodiment of a lead with segmented electrodes and a microelectrode, according to the invention.
Figure 27:
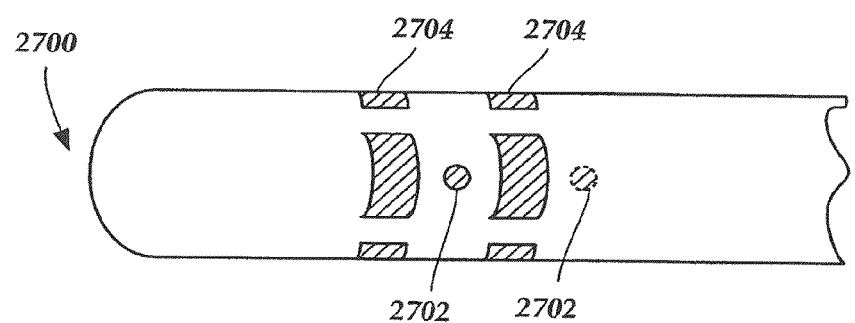
FIG. 27 is a schematic side view of a portion of an embodiment of a lead with segmented electrodes and microelectrodes, according to the invention.
Figure 28:
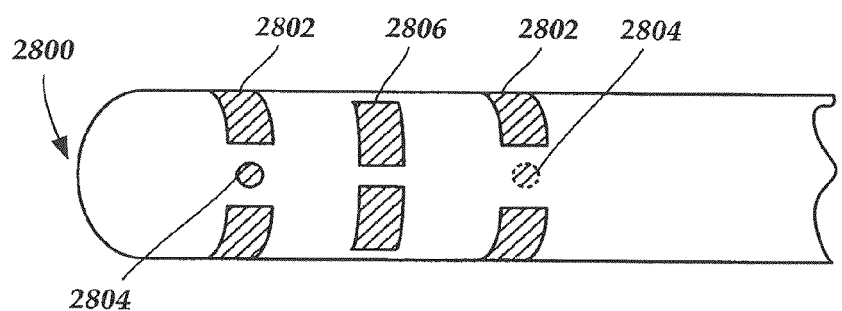
FIG. 28 is a schematic side view of a portion of another embodiment of a lead with segmented electrodes and microelectrodes, according to the invention.

Leads can also include one or more microelectrodes having a surface area that is substantially smaller than any single, segmented electrode. FIG. 26 schematically illustrates one embodiment of a lead 2600 with microelectrode 2602 disposed at a tip of the lead and five groups of segmented electrodes 2604 with three segmented electrodes per group. FIG. 27 schematically illustrates one embodiment of lead 2700 with two microelectrodes 2702 (the microelectrode with a dotted outline is on the opposite side of the lead) and two groups of segmented electrodes 2704 with three segmented electrodes per group. FIG. 28 schematically illustrates one embodiment of lead 2800 with two groups of two segmented electrodes 2802 that are ganged together, two microelectrodes 2804 (the microelectrode with a dotted outline is on the opposite side of the lead) with each microelectrode disposed between the two segmented electrodes of one of the two groups, and one group of four segmented electrodes 2806. It will be recognized that the microelectrodes may be positioned between the groups of segmented electrodes as illustrated in FIG. 27; between the electrodes of a group of segmented electrodes as illustrated in FIG. 28; proximal to all of the segmented electrodes; distal to all of the segmented electrodes; or any combination thereof (when there is more than one microelectrode). It will be recognized that one or more microelectrodes can be added to any of the other embodiments disclosed herein.

It will also be understood that in all of these embodiments, the electrodes do not need to be aligned along the longitudinal axis of the lead. The electrodes of one group may be radially staggered with respect to electrodes of one or more of the or more of the other groups as shown, for example, in FIG. 2 where the middle groups of segmented electrodes 130 are staggered and not aligned linearly along the longitudinal axis of the lead 100.

The electrodes can have any suitable size or shape and may be segments, rings, or cylindrical in shape. It will also be understood that the electrodes can have the same shape or size (or both shape and size) or that the shape or size (or both shape and size) of the electrodes may be different. The shape(s) of the electrodes may be regular or irregular. It will be recognized that even within a circumferential group the segmented electrodes may have different shapes or sizes (or both different shapes and sizes).

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by United States Letters Patent is:

1. An implantable stimulation lead, comprising:
a lead body having a longitudinal surface, a proximal end and a distal end; and
a plurality of electrodes disposed along the longitudinal surface of the lead body near the distal end of the lead body, the plurality of electrodes comprising:
a first ring electrode disposed at a first longitudinal position along the lead body,
a first set of segmented electrodes comprising at least three segmented electrodes disposed around a circumference of the lead body at a second longitudinal position along the lead body,
a second set of segmented electrodes comprising at least three segmented electrodes disposed around a circumference of the lead body at a third longitudinal position along the lead body, and
a second ring electrode disposed at a fourth longitudinal position along the lead body, wherein the second and third longitudinal positions are between the first and fourth longitudinal positions;
wherein each of the plurality of electrodes is configured and arranged to be individually coupleable to different stimulation channels of a control module and to be independently programmable to provide current steering.

2. The lead of claim 1, wherein the first set of segmented electrodes consists of three segmented electrodes.

3. The lead of claim 2, wherein the second set of segmented electrodes consists of three segmented electrodes.

4. The lead of claim 1, wherein the first set of segmented electrodes and the second set of segmented electrodes have a same number of segmented electrodes.

5. The lead of claim 4, wherein the segmented electrodes of the first set are aligned with the segmented electrodes of the second set along the longitudinal surface of the lead body.

6. The lead of claim 4, wherein the segmented electrodes of the first set are staggered with respect to the segmented electrodes of the second set along the longitudinal surface of the lead body.

7. The lead of claim 1, wherein the lead is configured and arranged for implantation in a brain of a human.

8. An implantable stimulation system, comprising:
the lead of claim 1; and
a control module coupleable to the lead.

9. The implantable stimulation system of claim 8, wherein the control module is a constant-current device.

10. An implantable stimulation lead, comprising:
a lead body having a longitudinal surface, a proximal end and a distal end; and
a plurality of electrodes disposed along the longitudinal surface of the lead body near the distal end of the lead body, the plurality of electrodes comprising:
a tip electrode disposed at, and covering, the distal end of the lead body,
a first set of segmented electrodes comprising at least three segmented electrodes disposed around a circumference of the lead body at a first longitudinal position along the lead body, and
a second set of segmented electrodes comprising at least three segmented electrodes disposed around a circumference of the lead body at a second longitudinal position along the lead body;
wherein each of the plurality of electrodes is configured and arranged to be individually coupleable to different stimulation channels of a control module and to be independently programmable to provide current steering.

11. The lead of claim 10, wherein the plurality of electrodes further comprises a ring electrode disposed at a third longitudinal position along the lead body.

12. The lead of claim 11, wherein the third longitudinal position is proximal to the first and second longitudinal positions along the lead body.

13. The lead of claim 11, wherein the tip electrode has a surface area larger than at least one of the segmented electrodes of the first set of segmented electrodes.

14. The lead of claim 11, wherein the lead is configured and arranged for implantation in a brain of a human.

15. The lead of claim 11, wherein the first set of segmented electrodes consists of three segmented electrodes.

16. The lead of claim 15, wherein the second set of segmented electrodes consists of three segmented electrodes.

17. An implantable stimulation system, comprising:
   the lead of claim 10; and
   a control module coupleable to the lead.

18. The implantable stimulation system of claim 17, wherein the control module is a constant-current device.

19. A method for brain stimulation, the method comprising:
   inserting the lead of claim 1 into a brain of a human;
   coupling the lead to a control module; and
   generating electrical signals, using the control module, at one or more of the plurality of electrodes to stimulate at least one target neuron of the brain.

20. A method for brain stimulation, the method comprising:
   inserting the lead of claim 10 into a brain of a human;
   coupling the lead to a control module; and
   generating electrical signals, using the control module, at one or more of the plurality of electrodes to stimulate at least one target neuron of the brain.

* * * * *